United States Patent
Camara y Ferrer et al.

(10) Patent No.: US 6,507,788 B1
(45) Date of Patent: Jan. 14, 2003

(54) RATIONAL SELECTION OF PUTATIVE PEPTIDES FROM IDENTIFIED NUCLEOTIDE, OR PEPTIDE SEQUENCES, OF UNKNOWN FUNCTION

(75) Inventors: Jose Antonio Camara y Ferrer, Paris (FR); Christophe Alain Thurieau, Paris (FR); Jean Martinez, Saussan (FR); Gilbert Bergé, Montpellier (FR); Catherine Gozé, Montpellier (FR)

(73) Assignees: Société de Conseils de Recherches et d'Applications Scientifiques (S.C.R.A.S.) (FR); Centre National de la Recherche Scientifique (C.N.R.S) (FR)

(*) Notice: Subject to any disclaimer, the term of this patent is extended or adjusted under 35 U.S.C. 154(b) by 0 days.

(21) Appl. No.: 09/257,525

(22) Filed: Feb. 25, 1999

(51) Int. Cl.[7] ............ C12Q 1/68; A01N 61/00; A61K 38/00; C07H 21/00; G01N 33/48
(52) U.S. Cl. ............ 702/19; 435/6; 536/23.1; 514/2; 530/300
(58) Field of Search ............ 702/19–27; 435/6; 536/23.1, 24.1; 514/2–12; 530/300–350

(56) References Cited

U.S. PATENT DOCUMENTS

| | | | |
|---|---|---|---|
| 4,708,934 A | | 11/1987 | Gillgan et al. |
| 4,917,999 A | | 4/1990 | Byng et al. |
| 5,360,727 A | | 11/1994 | Matsuo et al. |
| 5,472,945 A | * | 12/1995 | Schmaier ............ 514/12 |
| 5,523,208 A | | 6/1996 | Kohler et al. |
| 5,577,249 A | | 11/1996 | Califano |
| 5,671,090 A | | 9/1997 | Pernick et al. |
| 5,701,256 A | | 12/1997 | Marr et al. |
| 5,706,498 A | | 1/1998 | Fujimiya et al. |
| 5,756,295 A | | 5/1998 | Onda et al. |
| 5,856,928 A | | 1/1999 | Yan |
| 5,871,995 A | | 2/1999 | Iida et al. |
| 5,873,052 A | | 2/1999 | Sharaf |
| 5,873,082 A | | 2/1999 | Noguchi |
| 6,023,659 A | * | 2/2000 | Seilhamer et al. ............ 702/19 |
| 6,124,438 A | * | 9/2000 | Sutcliffe ............ 530/387 |

FOREIGN PATENT DOCUMENTS

| | | | |
|---|---|---|---|
| FR | PCT/FR98/01767 | | 3/1999 |
| WO | 96/41540 | * | 12/1996 |
| WO | 97/11964 | * | 3/1997 |
| WO | 99 10361 | | 4/1999 |

OTHER PUBLICATIONS

Bairoch et al., "The PROSITE database, its status in 1997", Nucleic Acids Research, 1997, vol. 25 No. 1 pp. 217–221.*
:Gerhold et al.[BioEssays, vol. 18, No. 12, pp. 973–981 1996)].*
Wells et al.[Journal of Leukocyte Biology, vol. 61, No. 5, pp. 545–550 (1997)].*
Russell et al.[Journal of Molecular Biology, vol. 244, pp. 332–350 (1994)].*
Keele et al. J Computational Biol. 1(1) 1994, pp. 65–76.*
Matsubara et al. Current Opinion in Biology vol. 4 pp. 672–677 (1993).*
Green et al. Science vol. 259 No. 5102 pp. 1356–1358 (1995).*
Fickett et al. Trends in Genetics vol. 12 No. 8 pp. 316–320 (1996).*
Nevill–Manning et al., Highly Specific Protein Sequence Motifs for Genome Analysis, *Proc. Natl. Acad. Sci. USA*; May 1998; vol. 95, pp. 5865–5871.
Bairoch et al., "The Swiss–PROT Protein Sequence Data Bank and Its Supplement TrEMBL", *Nucleic Acids Research*, 1997, vol. 25, No. 1, pp. 31–36.
Alan F. Bradbury and Derek G. Smyth, Peptide Amidation, TIBS 16: 112–115, Mar. 1991.
Andreas G. Katopodis, Dongsheng Ping, Christine e. Smith and Sheldon W. May, Functional and Structural Characterization of Peptidylamidoglyconate Lyase, the Enzyme Catalyzing the Second Step in Peptide Amidation, Biochemistry, vol. 30, No. 25: 6189–6194, Jun. 1991.
"SWISS–PROT+TREMBL!" Trends in Genetics, NL, Elsevier Science Publishers B.V., Amsterdam, vol. 13, No. 10, Oct. 1, 1997, p. 417.
Kerlavage A.R., et al., "Data Management and Analysis for High–Throughput DNA Sequencing Projects", IEEE Engineering in Medicine and biology Magazine, U.S. IEEE Inc., New York, vol. 14, No. 6, Nov. 1, 1995, pp. 710–717.

* cited by examiner

*Primary Examiner*—Marianne P. Allen
*Assistant Examiner*—Monika Sheinberg
(74) *Attorney, Agent, or Firm*—Hunton & Williams

(57) ABSTRACT

A method for identifying putative peptides of a given function from among nucleotide or peptide sequences of unknown function comprising the steps of:

(i) obtaining a polynucleotide or polypeptide database;
(ii) screening the database for the presence of a combination of nucleotides or amino acids indicative of the peptide of given function;
(ii) identifying the polynucleotide or polypeptide sequences which comprise the combination of nucleotides or amino acids indicative of the peptide of given function.

11 Claims, No Drawings

SEQUENCE LISTING

```
<160> NUMBER OF SEQ ID NOS:   10

<210> SEQ ID NO 1
<211> LENGTH: 12
<212> TYPE: PRT
<213> ORGANISM: unknown
<220> FEATURE:
<223> OTHER INFORMATION: Sequence origin:  dbEST

<400> SEQUENCE: 1

Cys Gln Asp Ser Ile Glu Pro Val Pro Gly Gln Lys
1               5                   10

<210> SEQ ID NO 2
<211> LENGTH: 8
<212> TYPE: PRT
<213> ORGANISM: unknown
<220> FEATURE:
<223> OTHER INFORMATION: Sequence origin:  pre-pro-bradykinine

<400> SEQUENCE: 2

Tyr Ala Arg Val Gln Val Val Ala
1               5

<210> SEQ ID NO 3
```

```
<211> LENGTH: 15
<212> TYPE: PRT
<213> ORGANISM: unknown
<220> FEATURE:
<223> OTHER INFORMATION: Sequence origin:  pre-pro-bradykinine

<400> SEQUENCE: 3

Phe Lys Ile Asp Asn Val Lys Lys Ala Arg Val Gln Val Val Ala
1               5                  10                  15

<210> SEQ ID NO 4
<211> LENGTH: 7
<212> TYPE: PRT
<213> ORGANISM: unknown
<220> FEATURE:
<223> OTHER INFORMATION: Sequence origin:  gene HYAA

<400> SEQUENCE: 4

Pro Leu Glu Pro Ser Gly Gly
1               5

<210> SEQ ID NO 5
<211> LENGTH: 15
<212> TYPE: PRT
<213> ORGANISM: unknown
<220> FEATURE:
<223> OTHER INFORMATION: Sequence origin:  gene HYA22

<400> SEQUENCE: 5

Glu Leu Gly Arg Gly Pro Gly Pro Leu Pro Glu Arg Gly Ala
1               5                  10                  15

<210> SEQ ID NO 6
<211> LENGTH: 18
<212> TYPE: PRT
<213> ORGANISM: unknown
<220> FEATURE:
<223> OTHER INFORMATION: Sequence origin:  glial cell line derived
      neurotrophic factor

<400> SEQUENCE: 6

Tyr Glu Arg Asn Arg Gln Ala Ala Ala Ala Asn Pro Glu Asn Ser Arg
1               5                  10                  15

Gly Lys

<210> SEQ ID NO 7
<211> LENGTH: 239
<212> TYPE: DNA
<213> ORGANISM: Homo sapiens
<220> FEATURE:
<221> NAME/KEY: Unsure
<222> LOCATION: (200)..(200)
<223> OTHER INFORMATION: unsure

<400> SEQUENCE: 7
ttcatgctca tgtaaccttc ttaatagtgc cttgtctgct gggtttgtag ctgtaagagt     60
tctgcaaact ggccctataa aaatattgat gctgtccatt aaaatgaatc tctctctctc    120
actcagtctc tctctctgtc tgtctctctt tcttctctct cctgccatgt gtgtgtctct    180
ctctactcct ctgattttgn cctctctctc tattctgcta ctctctctcc tctcctccg    239

<210> SEQ ID NO 8
<211> LENGTH: 62
<212> TYPE: PRT
<213> ORGANISM: Salmonella typhimurium
```

```
<400> SEQUENCE: 8

Met Lys Phe Thr Val Glu Arg Glu His Leu Leu Lys Pro Leu Gln Gln
1               5                   10                  15

Val Ser Gly Pro Leu Gly Gly Arg Pro Thr Leu Pro Ile Leu Gly Asn
            20                  25                  30

Leu Leu Leu Gln Val Ala Asp Gly Ala Leu Ser Leu Thr Gly Thr Asp
            35                  40                  45

Leu Glu Met Glu Met Val Ala Arg Val Thr Leu Ser Gln Pro
    50                  55                  60

<210> SEQ ID NO 9
<211> LENGTH: 609
<212> TYPE: PRT
<213> ORGANISM: Heliobacillus mobilis

<400> SEQUENCE: 9

Met Ala Thr Ala Asp Ala Ala Phe Asn Pro Arg Ala Gln Val Phe Glu
1               5                   10                  15

Trp Phe Lys Asp Lys Val Pro Ala Thr Arg Gly Ala Val Leu Lys Ala
            20                  25                  30

His Ile Asn His Leu Gly Met Val Ala Gly Phe Val Ser Phe Val Leu
            35                  40                  45

Val His His Leu Ser Trp Leu Ser Asp Gln Val Leu Phe Ala Pro Thr
    50                  55                  60

Pro Ile Phe Tyr Ala Arg Leu Tyr Gln Leu Gly Leu Asp Ala Ser Ala
65              70                  75                  80

Arg Ser Ala Asp Ala Leu Met Val Ala Arg Leu His Leu Pro Ala Ala
            85                  90                  95

Ile Ile Phe Trp Ile Ile Gly His Ile Lys Thr Pro Arg Glu Asp Glu
            100                 105                 110

Phe Leu Lys Asn Val Thr Phe Gly Lys Thr Leu Val Ala Gln Phe His
            115                 120                 125

Phe Leu Ala Leu Val Ala Thr Leu Trp Gly Met His Met Ala Tyr Ile
            130                 135                 140

Gly Val Arg Gly Ala Asn Gly Gly Ile Val Pro Thr Gly Leu Ser Phe
145             150                 155                 160

Asp Met Phe Gly Pro Ile Thr Gly Ala Thr Leu Ala Gly Asn His Val
            165                 170                 175

Ala Phe Gly Ala Leu Leu Phe Leu Gly Gly Val Phe His Phe Ala
            180                 185                 190

Gly Phe Asn Thr Lys Arg Phe Ala Phe Phe Glu Lys Asp Trp Glu Ala
            195                 200                 205

Val Leu Ser Val Ser Ala Gln Val Leu Ala Phe His Phe Ala Thr Val
            210                 215                 220

Val Phe Ala Met Ile Ile Trp Asn Arg Pro Asp Gln Pro Ile Leu Ser
225             230                 235                 240

Phe Tyr Phe Met Gln Asp Tyr Ala Leu Ser Asn Tyr Ala Ala Pro Glu
            245                 250                 255

Ile Arg Glu Ile Ala Ser Gln Asn Pro Gly Phe Leu Ile Lys Gln Val
            260                 265                 270

Ile Leu Gly His Leu Val Phe Gly Val Met Phe Trp Ile Gly Gly Val
            275                 280                 285

Phe His Gly Ala Ser Leu His Val Arg Ala Thr Asn Asp Pro Lys Leu
            290                 295                 300
```

```
Ala Glu Ala Leu Lys Asp Phe Lys Met Leu Lys Arg Cys Tyr Asp His
305                 310                 315                 320

Asp Phe Gln Lys Lys Phe Leu Ala Leu Ile Met Phe Gly Ala Phe Leu
            325                 330                 335

Pro Ile Phe Val Ser Tyr Gly Ile Ala Thr His Asn Thr Ile Ser Asp
            340                 345                 350

Leu His His Leu Ala Lys Ala Gly Met Phe Ala Asn Met Thr Tyr Ile
        355                 360                 365

Asn Ile Gly Thr Pro Leu His Asp Ala Ile Phe Gly Ser His Gly Thr
    370                 375                 380

Val Ser Asp Phe Val Ala Ala His Ala Ile Ala Gly Gly Leu His Phe
385                 390                 395                 400

Thr Met Val Pro Leu Trp Arg Met Val Phe Phe Ser Lys Val Ser Pro
            405                 410                 415

Trp Thr Thr Lys Val Gly Met Lys Ala Lys Arg Asp Gly Glu Phe Pro
            420                 425                 430

Cys Leu Gly Pro Ala Tyr Gly Gly Thr Cys Ser Ile Ser Leu Val Asp
        435                 440                 445

Gln Phe Tyr Leu Ala Ile Phe Phe Ser Leu Gln Val Ile Ala Pro Ala
    450                 455                 460

Trp Phe Tyr Leu Asp Gly Cys Trp Met Gly Ser Phe Val Ala Thr Ser
465                 470                 475                 480

Ser Glu Val Tyr Lys Gln Ala Ala Glu Leu Phe Lys Ala Asn Pro Thr
            485                 490                 495

Trp Phe Ser Leu His Ala Val Ser Asn Phe Thr Ser Glu Val Thr Ser
        500                 505                 510

Ala Thr Ser Ser Leu Lys Pro Leu Val Cys Ser Asn Thr Thr Met Val
    515                 520                 525

Thr Trp Phe Lys Pro Cys Trp Ala Ala His Phe Ile Trp Ala Phe Thr
    530                 535                 540

Phe Ser Met Leu Phe Gln Tyr Arg Gly Ser Arg Asp Glu Gly Ala Met
545                 550                 555                 560

Val Leu Lys Trp Ala His Glu Gln Val Gly Leu Gly Phe Ala Gly Lys
            565                 570                 575

Val Tyr Asn Arg Ala Leu Ser Leu Lys Glu Gly Lys Ala Ile Gly Thr
        580                 585                 590

Phe Leu Phe Phe Lys Met Thr Val Leu Cys Met Trp Cys Leu Ala Met
        595                 600                 605

Val

<210> SEQ ID NO 10
<211> LENGTH: 76
<212> TYPE: PRT
<213> ORGANISM: Streptomyces halstedii
<220> FEATURE:
<221> NAME/KEY: UNSURE
<222> LOCATION: (76)..(76)
<223> OTHER INFORMATION: unsure

<400> SEQUENCE: 10

Met Asn Ala Arg Ala Asp Arg Ala Gly Asp Thr Val His Arg Val Pro
1               5                   10                  15

Val Leu Val Val Gly Gly Ser Leu Val Gly Leu Ser Thr Ser Val Phe
            20                  25                  30

Leu Gly Arg Leu Gly Val Arg His Met Leu Val Glu Arg His Ala Gly
        35                  40                  45
```

```
Thr Ser Val His Pro Arg Gly Arg Gly Asn Asn Val Arg Thr Met Glu
    50                  55                  60

Val Tyr Arg Ala Ala Gly Val Glu Gln Gly Ile Xaa
65                  70                  75
```

RATIONAL SELECTION OF PUTATIVE PEPTIDES FROM IDENTIFIED NUCLEOTIDE, OR PEPTIDE SEQUENCES, OF UNKNOWN FUNCTION

BACKGROUND OF THE INVENTION (i) Field of the Invention

The present invention relates to a method for identifying putative peptides from nucleotide or peptide sequences of unknown function such as both nucleic acid and peptide precursors of a peptide comprising an amidated C-terminal end and, more particularly, to a method wherein putative precursor peptides are identified from a genetic database.

(ii) Description of Related Art

Certain combinations of nucleotides, when present in a polynucleotide, are known to give rise to certain properties in the polypeptide translated therefrom. One example includes those nucleotides which encode polypeptide hormone precursors which undergo a post-translation amidation reaction. Another example, as set forth in U.S. Pat. No. 4,917,999, relates to certain nucleotides which are characteristic of polypeptides exhibiting α-amylase enzymatic activity.

Amidated polypeptide hormones are synthesized in the form of a precursor which undergoes maturation. This maturation consists of an amidation reaction. The amidation reaction of the C-terminal end is a characteristic reaction of amidated polypeptide hormones. This reaction, which occurs on the precursor of one or more hormones, allows maturation of the hormone and also ensures its biostability in the physiological medium: the amide group formed is less vulnerable than the free acid function. The hormone is therefore more resistant to carboxypeptidases, it remains active in the cell for longer and retains an optimum affinity for its receptor site.

Amidation has been widely described ("Peptide amidation", Alan F. Bradbury and DerekG. Smyth, TIBS 16:112–115, March 1991 and "Functional and structural characterization of peptidylamidoglycolate lyase, the enzyme catalysing the second step in peptide amidation", A. G. Katopodis, D. S. Ping, C. E. Smith and S. W. May, Biochemistry, 30(25): 6189–6194, June 1991), and its mechanism is as follows:

1—Cleavage of the precursor polypeptide chain of the hormone by an endoprotease at the two basic amino acids, that is to say arginine and/or lysine, 2—Subsequently two cleavages by carboxypeptidase result, which lead to the extended glycine intermediate, 3—The enzyme PAM (peptidyl-glycine-amidating monooxygenase) comprises two distinct enzymatic activities: firstly, it converts the extended glycine intermediate into an α-hydroxyglycine derivative, the subunit of the enzyme PAM involved is PHM (peptidyl-glycine-hydrolylating monooxygenase). The derivative obtained serves as the substrate for the second subunit of PAM (called PAL: peptidyl-hydroxyglycine-amidating lyase), which fixes the amine function of the glycine on to the amino acid immediately adjacent to the N-terminal side and liberates glyoxylate.

This reaction involves the presence of a recognition site on the precursor of the hormone or hormones, a site which always comprises the sequence: glycine and two basic amino acids (arginine or lysine). The amidated polypeptide hormones which are to be secreted outside the endoplasmic reticulum are known to comprise a consensus signal sequence of about fifteen to thirty amino acids, this sequence being present at the N-terminal end of the polypeptide chain. It is cut later by a signal peptidase enzyme such that it is no longer found in the protein once secreted.

Given the importance of known amidated polypeptides in the context of numerous biological systems, methods have been sought for the identification of additional amidated polypeptides. Unfortunately, at the present time, the discovery of a new protein is not easy.

To date, the art has developed certain approaches in an attempt to identify novel proteins of potential biological interest.

In one approach, potentially new proteins of interest are isolated from a source by selecting a specific property which the researcher believes will be possessed by one or more potential proteins of interest in a sample. According to this approach, proteins can be isolated and purified by various techniques: precipitation at the isoelectric point, selective extraction by certain solvents and then purification by crystallization, counter-current distribution, adsorption, partition or ion exchange chromatography, electrophoresis.

The conventional protein isolation techniques described above provide only limited success in the isolation and identification of new biological molecules of interest. This approach implies knowledge of the properties of the protein to be isolated. Typically, one of two situations arises based on isolation of proteins using a common property. In the first situation, the common property will be for the most part unrelated or only marginally related to the biological function of the molecules being isolated. One could envision, for example, two proteins sharing identical isoelectric points but having completely unrelated biological functions. In the second situation, separation might be achieved based on common property which is very closely related to the biological function of the molecule being isolated. In this category, for example, one might envision molecules which bind to the same receptor molecule. In the former situation, the isolation of potentially new polypeptides is quite unfocussed given its likelihood of isolating compounds of completely unrelated biological function. By complete contrast, the latter situation suffers the exact opposite deficiency in that it enables isolation of only a very limited number of new biologically interesting molecules.

Thus, a person skilled in the art seeking to isolate potentially new polypeptides of interest by conventional protein separation techniques was confronted with the dilemma of obtaining a hodgepodge of biologically unrelated polypeptides or, alternatively, only a very specific set of polypeptides.

Another serious shortcoming of conventional techniques for isolation of new polypeptides from a sample relates to the nature of the sample itself. Obviously, there will be a limited number of available polypeptides for isolation and identification in any given biological sample. Furthermore, great care must be taken with such samples to ensure the continued integrity of the biologically active molecules therein.

Not surprisingly, previous attempts to isolate and characterize new peptides comprising an amidated C-terminal end have followed the conventional approach of starting with a biological sample and choosing from the arsenal of known separation techniques for isolating and identifying the peptides. For example, in U.S. Pat. No. 5,360,727 in the name of Matsuo et al., there was isolated a C-terminal alpha-amidating enzyme of porcine origin by extracting and purifying the enzyme from porcine atrium cords exhibiting the enzyme activity. In U.S. Pat. No. 5,871,995 issued in the name of Iida et al., purified enzymes participating in C-terminal amidation were purified from a biological material such as horse serum by affinity chromatography using a peptide C-terminal glycine adduct as a ligand. In U.S. Pat. No. 4,708,934 in the name of Gilligan et al., peptidylglycine alpha.-amidating monooxygenase enzyme was extracted from medullary thyroid carcinoma cell lines and tissue samples. Where identification of substantial numbers of new polypeptides capable of amidation is the goal, conventional isolation techniques such as these are completely unsuitable, as they typically permit isolation of only a single polypeptide of interest from a source suspected to contain that polypeptide.

In PCT/FR98/01767, the assignee of the present application has recently developed a method which overcomes many of disadvantages discussed above in that it enables the rapid identification of a large number of putative peptides which comprise an amidated C-terminal end. In particular, unlike earlier techniques which relied on a particular physical property of the polypeptide to isolate it from a source suspected or known to contain it, the method developed by the assignee relies on a characteristic of the peptide sequence of the precursor of all amidated hormones known to date, thereby allowing simultaneous detection of several new hormones of this category. More particularly, this technique relies on the direct identification of the nucleotide sequence which codes for the precursors in cDNA banks prepared from tissues in which the precursors of these hormones can be synthesized.

The method of PCT/FR98/01767 permits identification of the precursor of a peptide having an amidated C-terminal end, by the following successive stages:

1—Obtaining of a DNA bank;
2—Hybridization of one or more oligonucleotides OX with the DNA bank;
3—Identification of the DNA sequence or sequences of the bank which hybridizes with an oligonucleotide OX;
4—Identification in this sequence or sequences of one or more peptides with a possible amidated C-terminal end.

OX is a single-stranded oligonucleotide which can hybridize under mild conditions with an oligonucleotide OY of the sequence Y1-Y2-Y3-Y4-Y5, in which Y1 represents a nucleotide sequence of 1 to 12 nucleotides or Y1 is suppressed, Y2 represents a trinucleotide which codes for Gly, Y3 and Y4 independently represent a trinucleotide which codes for Arg or Lys and Y5 represents a nucleotide sequence of 1 to 21 nucleotides or Y5 is suppressed.

Preferably, the DNA bank is a cDNA bank. A cDNA bank contains the cDNA corresponding to the cytoplasmic mRNA extracted from a given cell. The bank is called complete if it comprises at least one bacterial clone for each starting mRNA. Hybridization takes place if two oligonucleotides have substantially complementary nucleotide sequences, and they can combine over their length by establishing hydrogen bonds between complementary bases.

The search by this method of PCT/FR98/01767 has been found to be much less restricting than the abovementioned conventional techniques of biochemistry, since:

it can lead to the isolation of several distinct precursors present in the same tissue by the same principle;
it allows detection, under the same technical conditions, of precursors corresponding to hormones which have very different biochemical and biological properties;
it allows concomitant identification of all the peptide hormones which can be contained in the same precursor.

As a result, the screening technique set forth in PCT/FR98/01767 allows a not insignificant saving in time and money in a sector where the costs of research and development represent a very high proportion of turnover.

By allowing the obtaining of a large number of potentially therapeutically useful polypeptides, the technique developed allows pharmacological study of active substances having a fundamental physiological roll in the mammalian organism: hormones and more particularly amidated polypeptide neurohormones. Having available for the first time cDNA corresponding to active substances, it is now possible to introduce the cloned vector by genetic engineering to lead to synthesis of hormones having a therapeutic use by means of microorganisms.

Although giving rise to numerous significant advantages in terms of the ability to rapidly obtain a large number of putative candidate peptide molecules which serve as precursors to peptides comprising an amidated C-terminal end, there are nonetheless still certain difficulties attendant with the use of a cDNA bank for carrying out the screening. As discussed earlier, the cDNA bank typically derives from a single cell and therefore will contain only those polypeptides which are expressed in that cell. This means that even if within the genome of the cell, the screening method will not detect a putative peptide if that peptide is not expressed in that cell. Furthermore, even to the extent that a polypeptide of interest is expressed in the cell, the screening technique is necessarily limited to polypeptides expressed by that particular cell and, indeed, by the particular species of life from which the cell is derived. This makes it difficult to screen for the vast numbers of putative peptides which are of interest.

Thus, the method of the PCT/FR98/01767 solved a very important restriction in the identification of putative peptides serving as precursors of peptides comprising an amidated C-terminal end. More specifically, while the method of PCT/FR98/01767 certainly provides the means through which to probe a cDNA bank for all possible sequences having the desired post-translational amidation property, it nonetheless was restricted to those cDNAs found in the cDNA bank.

Recently, there has been an interest in using available databases containing vast numbers of nucleotide sequences in order to, for example, compare a sequence of interest with known sequences.

For example, in U.S. Pat. No. 5,706,498, there is disclosed a gene database retrieval system for making a retrieval for a gene sequence having a sequence similar to a sequence data from a gene database. The gene database stores the sequence data of genes whose structures or sequences have already been analyzed and identified. The system includes a dynamic programming operation unit for determining the degree of similarity between target data and key data by utilizing the sequence data of the bases of the gene from the gene database as the target data and the sequence data of the bases as the key for retrieval, and a central processing device unit for executing the access process to make access to the gene database, in parallel to the operation process for determining the degree of similarity by transmitting the sequence data of the bases from the gene database continually one after another into the dynamic programming operation unit as the target data, by controlling the gene database and the dynamic programming operation unit.

U.S. Pat. No. 5,873,082 discloses a sequence database search wherein a homologous sequence of a given sequence is searched from the sequence database and the results outputted in order of higher homology. According to the patent, a plurality of lists having similarities and differences can be effectively compared. In the case of the sequence database search results, a large number of lists including a huge number of sequence names can be quickly compared.

In U.S. Pat. No. 5,577,249, there is disclosed a method for finding a reference sequence in a database. The most preferred embodiment has specific application to searching the genome of living organisms, in particular the human genome, to find locations and purposes of nucleotide sequences and other biological information that are found on strings of DNA. The method employs human genome databases commercially available which have substrings of the DNA chains broken down into nucleotide token sequences. A unique original index associated with the original DNA string is then created. A reference nucleotide sequence is selected. The reference indexes and original indexes are compared. The method was applied to match reference strings of nucleotides for the genome of *E. coli* which contains approximately 4 million nucleotides.

U.S. Pat. No. 5,701,256 discloses a method and apparatus for sequence comparisons wherein new proteins sequences are compared with known sequences, such as from a sequence database, typically with a view to determine what level of similarity is shared between the proteins in terms of structural and functional characteristics.

U.S. Pat. No. 5,523,208 discloses a method for scanning nucleotide or DNA sequence date banks to identify genetic regions or genes coding for biologically interacting proteins. In particular, the method provides a means of scanning data banks consisting of cloned genetic material, including but not limited to DNA, RNA, mRNA, tRNA and nucleotide fragments, to identify the function of genetic material of unknown function. The method, when used on DNA fragments of unknown coding potential will produce a list of gene fragments which code for proteins having the potential to form complexes or multimeric configurations with the unknown protein.

As the above discussion demonstrates, one of the major applications for computerized methods of searching databases of genetic information is the comparison of a newly found sequence of unknown function with a database of sequences of known function. The goal of such methods of course is to ascertain the function of the unknown protein by relating it to structurally similar proteins of known function. Another application of computerized methods is to find those sequences in a database which are structurally related. Still further methods try to find sequences which form complexes with a known sequence. The focus of all of these methods is generally on comparison of one sequence with another sequence with a view to determining which sequences are structurally similar, rather than determining which genes, from among a large database of genes, possesses a given biological property even where such genes are generally not structurally similar.

SUMMARY AND OBJECTS OF THE INVENTION

The present invention has as its primary objective the overcoming of the disadvantages attendant with prior art techniques for identifying biologically interesting molecules from among a large group of candidate molecules. This objective is achieved by providing a method for identifying putative peptides of a given function from among nucleotide or peptide sequences of unknown function by screening a database for the presence of a particular combination of nucleotides or amino acids indicative of the peptides of given function.

It is a further object of the present invention to provide a method of identifying a putative peptide of a given function which is not limited to those peptides expressed in a particular biological source, for example because the protein is not expressed in that source.

It is another object of the present invention to provide a method of identifying a putative peptide of a given function which does not depend on physical properties of the peptide, such as isoelectric point or solubility, for the identification.

Yet another object of the present invention is to provide a method of identifying a putative peptide of a given function which is applicable to proteins which otherwise are biologically unrelated in their physical properties.

Still another object of the present invention is to provide a method of identifying a putative peptide of a given function from among candidate polypeptides which exhibit a very low degree of homology with each other.

Another object of the present invention is to provide a method of identifying a putative peptide of a given function which facilitates pharmacological study of active substances having a fundamental physiological role in an organism such as hormones and, more particularly, amidated polypeptide hormones.

Another object of the present invention is to provide a method of identifying a putative peptide of a given function which can be carried out with available genetic databases and available software.

Briefly described, these and other objects of the invention are achieved by providing a method for identifying putative peptides of a given function from among nucleotide or peptide sequences of unknown function comprising the steps of:

(i) obtaining a polynucleotide or polypeptide database;

(ii) screening said database for the presence of a combination of nucleotides or amino acids indicative of the peptide of given function;

(ii) identifying the polynucleotide or polypeptide sequences which comprise the combination of nucleotides or amino acids indicative of the peptide of given function.

In a preferred aspect, the present invention provides a method for identifying a precursor of a peptide comprising an amidated C-terminal end comprising the steps of:

(i) obtaining a polynucleotide or polypeptide database;

(ii) screening the database for the presence of a combination of nucleotides or amino acids indicative of the precursor of the peptide comprising the amidated C-terminal end;

(ii) identifying the polynucleotide or polypeptide sequences which comprise the combination of nucleotides or amino acids indicative of the precursor of the peptide comprising the amidated C-terminal end.

The database preferably comprises polynucleotide sequences and/or polypeptide sequences corresponding to the polynucleotide sequences and, optionally, accession numbers for the polynucleotide sequences. Where the polypeptide sequences are not available in the data base, they may be obtained by translating the polynucleotide sequences in said database. In a preferred embodiment, three different polypeptide sequences are obtained, corresponding to translation of three different reading frames of said polynucleotide sequences.

The database may further include annotational information relating to the polypeptide or polynucleotide sequences, such as at least one of origin, source, features and references for the sequences.

In screening the database, it is preferred to first locate the AUG start codon in a polynucleotide sequence and verify that no stop codon is present between the AUG start codon and the combination of nucleotides indicative of the precursor of the peptide comprising the amidated C-terminal end.

Once the step of identifying nucleotide or polypeptide sequences has been carried out, the identified sequences can be compared with sequences of known biological function and those identified sequences whose biological function is unknown selected. Alternatively, after the step of identifying nucleotide or polypeptide sequences has been carried out, the similarity of the selected sequences of unknown biological activity can be compared with sequences of known function and, if no similar sequence is found, the sequence of unknown biological activity selected for further investigation. If a similar sequence is found, the sequence of unknown biological activity can be selected as a candidate sequence exhibiting the putative function of the known similar sequence.

In one embodiment, the identified polypeptide sequence can be obtained and the properties of the polypeptide sequence evaluated.

The combination of nucleotides preferably comprises the sequence Y1-Y2-Y3-Y4-Y5, in which Y1 is a nucleotide sequence of 1 to 12 nucleotides or is suppressed, Y2 is a codon for Gly, Y3 and Y4 independently are codons for Arg or Lys and Y5 is a nucleotide sequence of 1 to 21 nucleotides or Y5 is suppressed.

With the foregoing as well as other objects, features and advantages of the invention that will become hereinafter apparent, the nature of the invention may be better understood by reference to the Detailed Description of the Preferred Embodiments and to the appended claims.

DETAILED DESCRIPTION OF PREFERRED EMBODIMENTS

By "putative peptides of a given function" is meant polypeptides which include a particular oligonucleotide sequence which is characteristic of a particular function shared by many proteins among a single species and/or among different species. In particular, certain oligonucleotide sequences have been found to be associated with certain types of proteins, such as C-terminal amindated hormones or amylases. The invention is applicable wherever there is an oligonucleotide sequence indicative of such a function.

By "precursor of a peptide comprising an amidated C-terminal end" is meant any of the precursor proteins which undergo an amidation reaction at the C-terminal end as described, for example, in Bradbury et al.

By "polynucleotide or polypeptide database" is meant any of the publicly available databases, such as FASTA, GENBANK, PROSITE or SWISS-PROT which typically include polynucleotide and/or polypeptide sequence data. The nucleotide sequence data is available, for example, at EMBL, GENBANK and at other places such as EXPASY. Such data often will also include ACCESSION numbers.

If the peptide sequences corresponding to a given ACCESSION number are available (e.g., in SWISS-PROT), then this "validated" sequence is included in the database. Otherwise, the nucleotide sequence is preferably translated using programs available in the art such as Translate and/or Back-Translate. The translation is carried out using the data associated with the nucleotide sequence (3' or 5' end) and three different reading frames (N, N+1, N+2). If this information is not available, the translation is carried out using both the available nucleotide sequence and its complementary sequence (six putative peptides for a single nucleotide sequence).

Optionally, such database further includes annotations containing all of the information that is available for a particular sequence, such as ORIGIN, SOURCE, FEATURES, related REFERENCES and COMMENTS associated with the sequence. This facilitates further database mining. An example of the available for annotation is given below:

| | |
|---|---|
| LOCUS HUMXT00347 | 239 bp   mRNA   EST   24-JUN-1992 |
| DEFINITION | Human expressed sequence tag (EST00347 similar to Repeat: CT), mRNA sequence. |
| ACCESSION | M62275 |
| NID | g340398 |
| KEYWORDS | EST; expressed sequence tag. |
| SOURCE | *Homo sapiens* (library: Stratagene catalog #936205) female 2 yr old Hippocampus cDNA to mRNA. |
| ORGANISM | *Homo sapiens* |
| | Eukaryotae; *mitochondrial eukaryotes*; Metazoa; Chordata; |
| | Vertebrata; Eutheria; Primates; Catarrhini; Hominidae; Homo. |
| REFERENCE | 1 (bases 1 to 239) |
| AUTHORS | Adams, M. D., Kelley, J. M., Gocayne, J. D., Dubnick, M., |
| | Polymeropoulos, M. H., Xiao, H., Wu, A., Olde, B., Moreno, R. F., |
| | Kerlavage, A. R., McCombie, W. R. and Venter, J. C. |
| TITLE | Complementary DNA sequencing: Expressed sequence tags and human genome project |
| JOURNAL | Science 252, 1651–1656 (1991) |
| MEDLINE | 91262645 |
| FEATURES | Location/Qualifiers |
| source | 1..239 |
| | /organism="*Homo sapiens*" |
| | /db_xref="taxon:9606" |
| | /dev_stage="2 yr old" |
| | /sex="female" |
| | /tissue_type="Hippocampus" |
| | /tissue_lib="Stratagene catalog #936205" |
| BASE COUNT | 36 a   72 c   33 g   97 t   1 others |
| ORIGIN | |
| | 1 ttcatgctca tgtaaccttc ttaatagtgc cttgtctgct gggtttgtag ctgtaagagt |

-continued

```
 61 tctgcaaact ggccctataa aaatattgat gctgtccatt aaaatgaatc tctctctc
121 actcagtctc tctctctgtc tgtctctctt tcttctctct cctgccatgt gtgtgtctct
181 ctctactcct ctgattttgn cctctctctc tattctgcta ctctctctcc tctcctccg
SEQ ID NO: 7
```

By "combination of nucleotides or amino acids indicative of the precursor of the peptide comprising the amidated C-terminal end" is preferably meant the sequence Y1-Y2-Y3-Y4-Y5, in which Y1 is a nucleotide sequence of 1 to 12 nucleotides or is suppressed, Y2 is a codon for Gly, Y3 and Y4 independently are codons for Arg or Lys and Y5 is a nucleotide sequence of 1 to 21 nucleotides or Y5 is suppressed. The particular combination is set forth in detail in PCT/FR98/01767, the disclosure of which is hereby incorporated by reference.

In the preferred embodiment, the database to be screened is obtained by running the sql/plus script follows:

REFERENCE, COMMENT, FEATURES, BASECOUNT, SEQUENCE entries of the genbank data files.

The SOPHASE contains the reading frame (0, +1, +2) if the peptide sequence is generated using IHB's DNA translator, SOPEPTIDE contains the peptide sequence corresponding to a given SOACCESSION, finally SOPEPTIDEORIGIN tells how the peptide sequence have been obtained (IHB's DNA Translator, GENBANK, SWISS-PROT, ... ).

When a FASTA formatted file (see below) is used instead of a GENBANK formatted file, the header line is stored in the SODEFINITION field when we are dealing with a sequence of nucleotides and the nucleotidic sequence itself

```
-- ================================================================-- Nom de la
base : TGEN --   Name of SGBD       :   ORACLE Versian 7.0
--
--   ================================================================
--   ================================================================
--   Table : GBEST
--   ================================================================
drop table GBEST;
create table GBEST
(
     SODEFINITION              VARCHAR2 (500),
     SOACCESSION               VARCHAR2 (121)           not null,
     SOORGANISM                VARCHAR2 (500),
     SOSEQUENCE                LONG
) storage (initial 300M next 10M pctincrease 0);
--   ================================================================
--   Table : NUCSEQENV
--   ================================================================
drop table NUCSEQENV;
create table NUCSEQENV
(
     SOLOCUS                   VARCHAR2 (121),
     SOACCESSION               VARCHAR2 (121)           not null,
     SONID                     VARCHAR2 (121),
     SOSOURCE                  VARCHAR2 (2000),
     SOREFERENCE               VARCHAR2 (2000),
     SOCOMMENT                 VARCHAR2 (2000),
     SOFEATURES                VARCHAR2 (2000),
     SOBASECOUNT               VARCHAR2 (121),
) storage (initial 300M next 10M pctincrease 0);
--   ================================================================
--   Table : PEPSEQ
--   ================================================================
drop table PEPSEQ;
create table PEPSEQ
(
     SOACCESSION               VARCHAR2 (121)           not null,
     SOPHASE                   VARCHAR2 (1)
```

Obviously, the size of the different ORACLE fields can be adjusted in order to fit the size of the data that is being imported in the tables.

The SOLOCUS, SODEFINITION, SOACCESSSION, SOORGANISM, SONID, SOKEYWORDS, SOSOURCE, SOREFERENCE, SOCOMMENT, SOFEATURES, SOBASECOUNT, SOSEQUENCE fields in oracle contains respectively the LOCUS, DEFINITION, ACCESSSION, ORGANISM, NID, KEYWORDS, SOURCE, is stored in the SOSEQUENCE field. If the data being inserted in the database is a peptide sequence then the header line is stored in the SOPEPDEFINITION and the peptidic sequence is stored in the SOPEPTIDE field once again the SOPEPTIDEORIGIN will tell where the peptide sequence comes from (GENBANK, SWISS-PROT, ... ).

.gi|402336 (M17352) dnaN protein [*Salmonella typhimurium*]

MKFTVEREHLLKPLQQVSGPLG-
GRPTLPILGNLLLQVADGALSLTGTDLE-
MEMVARVTLSQP SEQ ID NO:8
>gi|306148 (Li19604) core polypeptide [*Heliobacillus mobilis*]
MATADAAFNPRAQVFEWFKDKVPATR-
GAVLKAHINHLGMVAGFVSFV-
LVHHLSWLSDQVLFAPTPIF-
YARLYQLGLDASARSADALMVARLHLPAAIIF
IIGHIKTPREDEFLKNVTFGKTLVAQFH-
FLALVATLWGMHMAYIGVRGANGGIVPT-
GLSFDMFGPITGATLAGNHVAFGALL-
FLGGVFHHFAGFNTKRFAFFEKDWEAVLSVSA
VLAFHFATVVFAMIIWNRPDQPILSFY-
FMQDYALSNYAAPEIREIASQNPGF-
LIKQVILGHLVFGVMFWIGGVFHGASLH-
VRATNDPKLAEALKDFKMLKRCYDHDFQKKF
LALIMFGAFLPIFVSYGIATHNTISDL-
HHLAKAGMFANMTYINIGTPLHDAIFG-
SHGTVSDFVAAHAIAGGLHFTMVPLWRM-
VFFSKVSPWTTKVGMKAKRDGEFPCLGPAYGG
TCSISLVDQFYLAIFFSLQVIAPAW-
FYLDGCWMGSFVATSSEVYKQAAELF-
KANPTWFSLHAVSNFTSEVTSATSSLK-
PLVCSNTTMVTWFKPCWAAHFIWAFTFSMLFQ
YRGSRDEGAMVLKWAHEQVGLGF-
AGKVYNRALSLKEGKAIGTFLFFKMTVL-
CMWCLAMV SEQ ID NO:9
>gi|153320 (L05390) hydroxylase [*Streptomyces haistedii*]
MNARADRAGDTVHRVPVLV-
VGGSLVGLSTSVFLGRLGVRHMLVER-
HAGTSVHPRGRGNNVRTMEVYRAAGVEQGIX. SEQ ID NO:10

In compiling the database for screening, standard file formats used to store "High Throughput Sequencing" programs and other "Genome" programs (e.g., FASTA, GENBANK) are read and manipulated. Then, the portions of data which are relevant for the screening step, e.g., the annotation data, are identified. The resulting fields are inserted into oracle. If the nucleotide sequence is a 5' end, the sequence is directly translated into a peptide sequence, if it is a 3' end, the complementary sequence of the given sequence is generated and is used for translation (the translation phase takes into account the three possible reading frames to generate the peptide sequence). The last step involves the prediction of the secondary structure of the peptide, which is based on information theory and was developed by J. Garnier, D. Osguthorpe, and B. Robson. The software uses all possible pair frequencies within a window of 17 amino acid residues. After cross validation on a data base of 267 proteins, the predication has a mean accuracy of 64.4% for a three state prediction (helix, beta strand, and coil). The program produces two outputs, one giving the sequence and the predicted secondary structure, the other giving the probability values for each secondary structure at each amino acid position. The predicted secondary structure is the one of highest probability compatible with a helix segment of at least four residues and a extended segment (beta strand) of at least two residues.

Once the relevant data has been assembled in the database, such database can be screened for the presence of a combination of nucleotides or amino acids indicative of the precursor of the peptide comprising the amidated C-terminal end. The purpose of this step of course is to convert the huge amount of unsorted data to a limited set of putative peptides of pharmaceutical interest (potential hormones or hormone fragments, or endogene receptor ligands and the like). The general description of the process is followed by an application to a search of potential amidated peptides in the Expressed Sequence Tags database.

The general process proceeds as follows:
retrieve automated sequences from a public source, such as the internet (EMBL, GENBANK, SWISS-PROT, PDB, etc.)
Analyze file and import data into ORACLE
Select sequences from a subset (e.g. GENBANK EST) or the entire database
search for all of the sequences exhibiting a specific motif of interest, such as precursors of a peptide comprising an amidated C-terminal end
Check that no STOP codon is present in between the AUG codon indicating the beginning of the reading frame and the sought motif;
Select the sequences of unknown biological function
Verify that, when found, the motif is an Open Reading Frame (Kozak consensus sequence)
Compare the environment of the motif location to the one required (e.g., secondary structures required around a maturation site such as the proximity of alpha
helices or beta-sheets.
Check for similarity of the sequences and other known sequences (DEFINITION field)
use threading techniques to search sequences displaying similar secondary structure if no similar structures are defined in the database
If no similar sequence is found, select the sequence as a synthetic candidate whose function has to be determined
If similar sequences of known function are found, the sequences can be selected as a synthetic candidate hose putative function is the one of the similar sequence.

The following examples are given by way of illustration and should in no way be construed as limiting the subject matter disclosed and claimed.

EXAMPLES

Using the method described above, the following peptides were identified and tested:
(See Table on Following Page)
The experimental conditions employed are now discussed.
Binding Assay: Alternative protocol by Skatron
The experimental conditions are identical throughout the binding assay protocols except that:
the volume R in operation is 200 µl
the test is carried out in 96 well Falcon plaques
the reaction is directly stopped by filtration on filterMat (ref. 11734) Skatron and the radioactivity associated with the filtrate is evaluated:
either directly with a γ counter for the peptides labelled with iodine 124:
or with a counter in the presence of 5 mL of scintillating liquid.

Membrane Preparations of Guinea Pig Brains and Binding Assay

The guinea pigs are sacrificed by rupturing their cervical vertibrae, decapitated, and the brains are removed very rapidly into a sucrose-Tris-HCl buffer (5 mM, 0.32 M, Tris-HCl, 0.1 g/l bacitracine) at 4° C. (about 10 mL of buffer per brain). The brains are then homogenized with a Potter and the homogenate is placed in incubation 30 minutes at 37° C. under agitation, then centrifuged twice for 35 minutes at 100,000×g at 4° C. The bottoms are placed in suspension in a minimum buffer containing 50 mM Tris-HCl and 5 mM $MgCl_2$, then are aliquoted and stored in liquid nitrogen. The protein content of the membrane preparations is evaluated according to the method of Bradford (BioRad, according to the manufacturers protocol).

APPENDIX B

SUMMARY OF RESULTS OF COMBINATION

| Peptide | Sequence | Origin | Tests of bonding With | Results |
|---|---|---|---|---|
| K2 | H-CQDSIEPVPGQK-NH2 (SEQ ID NO: 1) | dbEST | membranes of guinea pig brain<br>membranes of different organs of the rat<br>HeLa cells<br>Jurkat T cells | positive (IC50 = 100 $\mu$M0<br>negative<br>positive (IC50 = 3 $\mu$M)<br>negative |
| K3/YK3 | H-YARVQVVA-NH2 (SEQ ID NO: 2) | pre-pro-bradykinine | membranes of guinea pig brain<br>membranes of different organs of the rat<br>HeLa cells<br>Jurkat T cells | positive (IC50 = 90 $\mu$M)<br>positive (IC50 = 100 $\mu$M)<br>positive (IC50 = 6 $\mu$M)<br>positive (IC50 = 60 $\mu$M) |
| K3R | H-YFKIDNVKKARVQVVA-NH2 (SEQ ID NO: 3) | pre-pro-bradykinine | membranes of guinea pig brain<br>membranes of the brain/liver and different organs of the rat<br>HeLa cells<br>Jurkat T cells | positive (IC50 = 8 $\mu$M)<br>positive (IC50? 100 $\mu$M)<br>positive (IC50 = 2 $\mu$M)<br>positive (IC50 = 50 $\mu$M) |
| K4 | H-PLEPSGG-NH2 (SEQ ID NO: 4) | gene HYAA | membranes of guinea pig brain<br>membranes of different organs of the rat<br>HeLa cells<br>Jurkat T cells | positive (IC50 = 90 $\mu$M)<br>negative<br>positive (IC50 = 15 $\mu$M)<br>positive (IC50 = 100 $\mu$M) |
| K9 | H-ELGRGPGPPLPERGA-NH2 (SEQ ID NO: 5) | gene HYA22 | membranes of guinea pig brain<br>membranes of rat brain<br>membranes of different organs of the rat<br>HeLa cells<br>Jurkat T cells | positive (IC50 = 0.6 $\mu$M)<br>positive (IC50 = 90 $\mu$M)<br>positive (IC50? 100 $\mu$M)<br>Not determined<br>negative |
| K11 | H-YERNRQAAAANPENSRGK-NH2 (SEQ ID NO: 6) | glial cell line derived neurotrophic factor | membranes of guinea pig brain<br>membranes of rat brain<br>membranes of different organs of the rat<br>HeLa cells<br>Jurkat T cells | positive (IC50 = 50 $\mu$M)<br>positive (IC50 = 90 $\mu$M)<br>positive (IC50? 100 $\mu$M)<br>Not determined<br>negative |

Bonding of Labelled Agonists to the Guinea Pig Brain Membrane Preparation

The membranes are placed in a buffer (50 mM Tris-HCl, 5 mM MgCl$_2$ and 0.1 g/l bacitracine to the desired protein concentration (bond of iodized CCK), 0.1 mg of protein/ml; bond of iodized gastrine: 0.5 mg of proteins/ml). They are then incubated in the presence of a labelled ligand in a total volume of 500 $\mu$l (about 10 $\mu$M for the iodized CCK$_8$, 20 pM for the iodized gastrine,$_3$), 50–80 minutes at 25° C., and in the presence or absence of cold agonists. The reaction is stopped with 3 mL of additional BSA buffer (20 g/l) at 4° C., the tubes are centrifuged at 10,000×g, the supernatant is drawn off and the radioactivity associated with the precipitate is evaluated with a gamma counter.

Bonding of Radiolabelled Agonists to Jurkat T Cells

Culture Conditions of the Cells of the Jurkat T Human Lymphocytic Line

The Jurkat cells are cultivated in an RPMI 1640 supplement medium in a fetal veal (10% volume/volume) and antibiotic (50 U/mL of penicillin and 50 $\mu$m/mL of streptomycin) serum in a humid incubator at 37° C. under an atmosphere of 5% CO$_2$ in the air.

Binding Assay

The cells are obtained by centrifugation (514 g, 5 minutes), then are washed twice in a standard medium containing: 98 mM NaCl; 6 mM Kcl; 2.5 mM NaH$_2$PO$_4$; 1.5 mM CaCl$_2$; 1 mM MgCl$_2$; 5 mM Na-pyruvate; 5 mM Na-fumarate; 5 mM Na-glutamate; 2 mM glutamine; 11.5 mM glucose; 24.5 mM Hepes (N-[2-hydroxyethyl] piperazine-N'-[2-ethane sulfonic acid]); 0.5 g/l bacitracine; 0.1 g/l Soybean Trypsin Inhibitor, pH 7.4.

The experiments of the bonds of agonists labelled with iodine 125 (about 50 picomolar) are carried out at 37° C. under agitation for 45–60 minutes in a final volume of 0.5 mL of standard medium containing 2×10$^6$ cells (4×10$^6$ cells/mL) and in the presence or absence of competitors. The reaction is stopped by addition of 2 mL of standard buffer at 4° C. supplemented with bovine serum albumin (BSA) (20 g/l), and 10 minutes of centrifugation at 10,000×g at 4° C. The radioactivity associated with the cellular precipitate is quantified with a gamma counter. The non-specific bond is evaluated in the presence of a micromolar concentration of cold homog peptide.

Membrane Preparations of different Rat Tissues and Organs

1) Rats are sacrificed by rupturing their cervical vertebrae, and the different tissues removed and washed several times in a large volume of NaCl 9 per thousand.

The following steps are carried at 4° C.

2) The tissues and organs are transferred, still separately, in a sucrose buffer containing:

0.25 M sucrose
25 mM TRIS-HCl, pH 7.4.
0.2 mM PMSF
0.1 mM, 1–10 phenantrolin
100 μg/mL STI They are then gently cut up with the aid of fine scissors and crushed using an ultraturax apparatus.

3) The tissues and organs are finally ground using a Potter apparatus: minimum of ten times in each rotational direction at a minimum of 1000 rpm.

4) The ground material is centrifuged at 500 g and for 10 minutes at 4° C. The supernatants are saved, the bottoms put again in the sucrose buffer and centrifuged again under the same conditions.

5) The 2 supernatants are then mixed and centrifuged at 100,000×g for 30 minutes at 4° C.

6) The supernatants are discarded and the bottoms placed again the the sucrose buffer for centrifuging a second time at 100,000×g for 30 minutes at 4° C.

7) The supernatants are discarded, and the bottoms placed again in a binding buffer containing 50 mM TRIS-HCl at pH 7.4 and 5 mM $MgCl_2$.

8) The content of proteins in the membrane suspensions is evaluated using a Bradford determination (Bradford, according to the protocol of the manufacturer). They are aliquoted and stocked in liquid nitrogen at −80° C.

The studies of the bonds are carried out according to a protocol identical to that used with the membranes of guinea pig brain.

Studies of the Labelled Agonists on the Hela Cell Line

The cells are cultivated in a DMEM medium supplemented with 10% fetal veal serum, 0.5% antibiotics (penicillin /streptomycin) and 0.5% glutamine.

24–48 hours before experimentation, the cells are replicated in 24-well laques with approximately 100,000 cells per well and per mL.

The bonding studies are carried out with a BindH buffer

| NaCl | 98 mM | 5.72 g/l |
|---|---|---|
| KCl | 6 mM | 0.45 g/l |
| $NaH_2PO_4$ | 2.5 mM | 0.3 g/l |
| Na-pyruvate | 5 mM | 0.55 g/l |
| Na-fumarate | 5 mM | 0.58 g/l |
| Na-glutamate | 5 mM | 0.84 g/l |
| $CaCl_2$ | 1.5 mM | 0.22 g/l |
| $MgCl_2$ | 1 mM | 0.20 g/l |
| HEPES | 25 mM | 6.07 g/l |
| glucose | 11.5 mM | 2.07 g/l |
| glutamine | 2 mM | 0.22 g/l |
| STI | | 0.1 g/l |

For the experiment, the medium is removed and the cells washed twice with 1 mL of buffer. The reaction medium (500 μL) containing the labelled agonist is added into each well in the presence or absence of the cold homolog agonist and the plaques are incubated one hour at 37° C.

The reaction is stopped by removal of the reaction volume and the wells are rinsed twice with 1 mL of BindH 20% BSA.

The cells are lysed with 500 μl of 1 N soda for 20 minutes at ambient temperature and the radioactivity associated with the lysate is evaluated with a gamma counter.

Although only preferred embodiments are specifically disclosed and claimed herein, it will be appreciated that modifications may be made to the preferred embodiments without departing from the spirit and intended scope of the invention.

What is claimed is:

1. A method for identifying a precursor of a peptide comprising an amidated C-terminal end comprising the steps of:
   (i) screening a nucleotide database for the presence of a Y1-Y2-Y3-Y4-Y5 sequence, wherein Y1 is a nucleotide sequence of 1 to 12 nucleotides or is suppressed, Y2 is a codon for Gly, Y3 and Y4 independently are codons for Arg or Lys, and Y5 is a nucleotide sequence of 1 to 21 nucleotides or Y5 is suppressed;
   (ii) identifying a polynucleotide sequence that comprises the Y1-Y2-Y3-Y4-Y5 sequence;
   (iii) determining a polypeptide encoded by the polynucleotide sequence to identify said precursor of the peptide comprising the amidated C-terminal end.

2. The method of claim 1, wherein said database comprises polynucleotide sequences and accession numbers for said polynucleotide sequences.

3. The method of claim 1, wherein said database comprises both polynucleotide sequences and polypeptide sequences corresponding to said polynucleotide sequences.

4. The method of claim 1, wherein said database further comprises annotational information relating to said polynucleotide sequences.

5. The method of claim 3, wherein said annotational information comprises at least one of origin, source, features and references for said sequences.

6. The method of claim 1, wherein said step of screening said database further comprises the steps of locating the AUG start codon in a polynucleotide sequence and verifying that no stop codon is present between said AUG start codon and the combination of nucleotides indicative of the precursor of the peptide comprising the amidated C-terminal end.

7. The method of claim 1, further comprising the step, after the step of identifying nucleotide sequences, of comparing said identified sequences with sequences of known biological function and selecting those identified sequences whose biological function is unknown.

8. The method of claim 7, further comprising the step of comparing the similarity of the selected sequences of unknown biological activity with sequences of known function and, if no similar sequence is found, selecting said sequence of unknown biological activity for further investigation.

9. The method of claim 7, further comprising the step of comparing the similarity of the selected sequences of unknown biological activity with sequences of known function and, if a similar sequence is found, selecting said sequence of unknown biological activity as a candidate sequence exhibiting the putative function of the known similar sequence.

10. A method for identifying a precursor of a peptide comprising an amidated C-terminal end comprising the steps of:
    (i) screening a polypeptide database for the presence of a polypeptide that is encoded by a nucleotide sequence comprising a Y1-Y2-Y3-Y4-Y5 sequence, wherein Y1 is a nucleotide sequence of 1 to 12 nucleotides or is suppressed, Y2 is a codon for Gly, Y3 and Y4 independently are codons for Arg or Lys and Y5 is a nucleotide sequence of 1 to 21 nucleotides or Y5 is suppressed;
    (ii) identifying a polypeptide encoded by the nucleotide sequence to identify said precursor of the peptide comprising the amidated C-terminal end,
    wherein said step of screening said database further comprises the steps of locating the AUG start codon in a polynucleotide sequence and verifying that no stop codon is present between said AUG start codon and the combination or nucleotides indicative of the precursor of the peptide comprising the amidated C-terminal end.

11. A method for identifying a precursor of a peptide comprising an amidated C-terminal end comprising the steps of:
    (i) obtaining a polynucleotide or polypeptide database;
    (ii) screening said database for the presence of a combination of nucleotide or amino acids indicative of the precursor of a peptide comprising an amidated C-terminal;
    (iii) identifying the polynucleotide or polypeptide sequences which comprise the combination of nucleotides or amino acids indicative of the precursor of a peptide comprising an amidated C-terminal;
    wherein said identified polypeptide sequence is SEQ ID NO: 1, SEQ ID NO: 2, SEQ ID NO: 3, SEQ ID NO: 4, SEQ ID NO: 5, or SEQ ID NO: 6.

* * * * *